United States Patent [19]
Franson et al.

[11] Patent Number: 5,591,456
[45] Date of Patent: Jan. 7, 1997

[54] MILLED NAPROXEN WITH HYDROXYPROPYL CELLULOSE AS A DISPERSION STABILIZER

[75] Inventors: Nancy M. Franson, Collegeville; Donald R. Snyder, Limerick, both of Pa.

[73] Assignee: NanoSystems L.L.C., Collegeville, Pa.

[21] Appl. No.: 386,790

[22] Filed: Feb. 10, 1995

[51] Int. Cl.[6] .............................. A61K 9/18; A61K 9/14
[52] U.S. Cl. .................. 424/494; 424/493; 424/499; 514/781; 514/951
[58] Field of Search ........................ 424/489, 494, 424/493, 499; 514/781, 951

[56] References Cited

U.S. PATENT DOCUMENTS 4,826,689  5/1989  Violanto et al. ..................... 424/489
5,145,684  9/1992  Liversidge et al. .................. 424/489

OTHER PUBLICATIONS

Cioli, et al., "Toxicological and Applied Pharmacology", vol. 50, 1979, pp. 283–289.
Price et al, "Drugs", 40 (Suppl. 5); 1–11, 1990.

*Primary Examiner*—James M. Spear
*Attorney, Agent, or Firm*—Rudman & Balogh

[57] ABSTRACT

Dispersible particles consisting essentially of crystalline NSAID having hydroxypropyl cellulose adsorbed on the surface thereof in an amount sufficient to maintain an effective average particle size of less than about 1000 nm. Pharmaceutical compositions containing the particles exhibit unexpectedly reduced gastric irritation following oral administration and/or hastened onset of action.

11 Claims, No Drawings

MILLED NAPROXEN WITH HYDROXYPROPYL CELLULOSE AS A DISPERSION STABILIZER

FIELD OF THE INVENTION

This invention relates to pharmaceutical compositions containing NSAIDs used as analgesics for mammals.

BACKGROUND OF INVENTION

Nonsteroidal anti-inflammatory drugs (NSAIDs) are one of the most commonly used and therapeutically effective groups of drugs. However, gastric irritation problems constitute the most frequently recognized adverse side effect following oral administration of NSAIDs. Such side effects are well recognized and must be weighed against the clinical efficacy of the drugs.

A great amount of research has been undertaken in an attempt to understand the underlying mechanism responsible for these effects. For example, Cioli et al, *Tox. and Appl. Pharm.*, 50, 283–289 (1979) suggest that gastrointestinal lesions in laboratory animals resulting from the oral administration of acidic NSAIDs may depend on two different mechanisms: a local action exerted by contact with the gastric mucosa and a generalized/centrally mediated (systemic) action, taking place following oral administration.

More recently, Price et al, *Drugs* 40 (Suppl. 5):1–11, 1990, suggest that NSAID-induced gastric damage occurs as a result of NSAID-mediated direct and indirect acidic damage followed almost simultaneously by the deleterious systemic effect of prostaglandin inhibition.

A variety of strategies have been used in the management of NSAID-induced gastric damage. These include: 1) the development and use of NSAIDs with less toxic potential; 2) the reduction or elimination of the agent that actually causes the injury; and 3) the enhancement of the mucosal defense. However, these approaches have not proven entirely successful.

For example, the most effective means of preventing gastric damage, i.e., by eliminating the primary aetiological agent is rarely feasible with NSAIDs inasmuch as patients with severe inflammatory disease are rarely able to cease using these drugs. Although selection of less toxic NSAIDs should prove useful, the only practical solution, at present, is to treat the NSAID induced gastric damage. Misoprostol (a methylated prostaglandin $E_1$) has been approved by the FDS for use in preventing NSAID gastropathy. However, Misoprostol is expensive, must be administered multiple times daily and can cause unacceptable side effects.

In copending U.S. application Ser. No. 07/897,193 filed Jun. 10, 1992, Now Abandoned the use of NSAID particles having a surface modifier adsorbed on the surface thereof in an amount sufficient to maintain an average particle size of less than about 400 nm was described as being useful in reducing gastric irritation in mammals.

It would be highly desirable to provide NSAID formulations that can exhibit an even greater reduction in gastric irritation and exhibiting greater enhanced onset of action as an analgesic.

SUMMARY OF THE INVENTION

It has been discovered that NSAID nanoparticles as described in U.S. application Ser. No. 07/897,193 now abandoned when accompanied by hydroxypropyl cellulose as a surface modifier exhibits unexpectedly superior reduced gastric irritation following oral administration as well as exhibiting hastened onset of analgesic activity.

More particularly, in accordance with this invention, there are provided particles consisting essentially of an NSAID having hydroxypropyl cellulose adsorbed on the surface thereof in an amount sufficient to maintain an average particle size of less than about 1000 nm.

This invention further provides a pharmaceutical composition comprising the above-described particles and a pharmaceutically acceptable carrier.

In another embodiment of the invention, there is provided a method of treating a mammal comprising administering to the mammal the above-described pharmaceutical composition.

In yet another embodiment of the invention, there is provided a method of preparing the above-described particles comprising the steps of dispersing an NSAID in a liquid dispersion medium and wet grinding the NSAID in the presence of rigid grinding media, wherein the pH of said medium is maintained within the range of from 2 to 6.

In further embodiments of the invention, there are provided methods of reducing gastric irritation and/or hastening the onset of action which include administering the above-described pharmaceutical composition to a mammal.

It is an advantageous feature of this invention that pharmaceutical compositions containing NSAIDs are provided which exhibit reduced gastric irritation following oral administration.

It is another advantageous feature of this invention that pharmaceutical compositions are provided exhibiting hastened onset of action.

It is another advantageous feature of this invention that the use of the particular surface modifier reduces adsorption variability.

Other advantageous features will become readily apparent upon references to the following description of preferred embodiments.

DESCRIPTION OF PREFERRED EMBODIMENTS

This invention is based on the discovery that nanoparticulates comprising an NSAID, for example naproxen, having its surface modified with hydroxypropyl cellulose demonstrates reduced gastric irritation and/or a more rapid onset of action following oral administration. While the invention is described herein primarily in connection with its preferred class of drugs, i.e., NSAIDs, it is also useful in conjunction with other classes of drug substances, e.g., antibiotics, quinolones, antilipemics and roentgenographics.

The particles of this invention comprise an NSAID. The NSAID exists as a discrete, crystalline phase. The crystalline phase differs from an amorphous or non-crystalline phase which results from conventional solvent precipitation techniques, such as described in U.S. Pat. No. 4,826,689. The NSAID can be present in one or more suitable crystalline phase.

The invention can be practiced with a wide variety of NSAIDs. However, the NSAID must be poorly soluble and dispersible in at least one liquid medium. By "poorly soluble" it is meant that the NSAID has a solubility in the liquid dispersion medium, e.g., water, of less than about 10 mg/ml, and preferably of less than about 1 mg/ml at processing temperature, e.g., room temperature. The preferred liquid dispersion medium is water. However the invention can be practiced with other liquid media in which the NSAID is poorly soluble and dispersible including, for example, aqueous salt solutions, safflower oil and solvents such as ethanol, t-butanol, hexane and glycol. The pH of the aqueous dispersion media can be adjusted by techniques known in the art.

The NSAIDs useful in the practice of this invention can be selected from suitable acidic and nonacidic compounds. Suitable acidic compounds include carboxylic acids and enolic acids. Suitable nonacidic compounds include, for example, nabumetone, tiaramide, proquazone, bufexamac, flumizole, epirazole, tinoridine, timegadine and dapsone.

Suitable carboxylic acid NSAIDs include, for example, salicylic acids and esters thereof, such as aspirin, diflunisal, benorylate and fosfosal; aceitc acids, including phenylacetic acids such as diclofenac, alclofenac and fenclofenac, and carbo- and heterocyclic acetic acids such as etodolac, indomethacin, sulindac, tolmetin, fentiazac and tilomisole; and propionic acids, such as carprofen, fenbufen, flurbiprofen, ketoprofen, oxaprozin, suprofen, tiaprofenic acids, ibuprofen, naproxen, fenoprofen, indoprofen, pirprofen; and fenamic acids, such as flufenamic, mefenamic, meclofenamic and niflumic.

Suitable enolic acid NSAIDs include, for example, pyrazolones such as oxyphenbutazone, phenylbutazone, apazone and feprazone, and oxicams such as piroxicam, sudoxicam, isoxicam and tenoxicam.

The above-described NSAIDs are known compounds and can be prepared by techniques known in the art.

In particularly preferred embodiments of the invention, the NSAID is naproxen, hetoprofin, indomethacin or ibuprofen, and particularly naproxen.

The particles of this invention contain an NSAID as described above having a hydroxypropyl cellulose adsorbed on the surface thereof.

I have discovered that hydroxypropyl cellulose, particularly hydroxypropyl cellulose having a viscosity range of 1 to 100 cps in a 3% solution in water preferably the viscosity to about 10 cps when used as a surface modifier for NSAIDs, in formulating nanoparticulate compositions unexpectedly results in enhanced resistance to gastric irritation as compared to that of other surface modifiers described in U.S. application Ser. No. 07/897,193 now abandoned. This particular property of the species of the genus of U.S. application Ser. No. 07/897,193 now abandoned has been heretofore unknown.

The hydroxypropyl cellulose is adsorbed on the surface of the NSAID in an amount sufficient to maintain an effective average particle size of less than about 400 nm. The surface modifier does not chemically react with the NSAID or itself. Furthermore, the individually adsorbed molecules of the surface modifier are essentially free of intermolecular crosslinkages.

As used herein, particle size refers to a number average particles size as measured by conventional particles size measuring techniques well known to those skilled in the art, such as sedimentation field flow fractionation, photon correlation spectroscopy, or disk centrifugation. By "an effective average particle size of less than about 1000 nm: is meant that at least 90% of the particles have a number average particle size of less than about 1000 nm when measured by the above-noted techniques. In preferred embodiments of the invention, the effective average particle size is less than about 400 nm. With reference to the effective average particle size, it is preferred that at least 95% and, more preferably, at least 99% of the particles have a particle size of less than the effective average, e.g., 400 nm. In particularly preferred embodiments, essentially all of the particles have a size less than 1000 nm.

The particles of this invention can be prepared in a method comprising the steps of dispersing an NSAID in a liquid dispersion medium and applying mechanical means in the presence of grinding media to reduce the particle size of the NSAID to an effective average particle size of less than about 1000 nm. The particles can be reduced in size in the presence of the surface modifier. Alternatively, the particles can be contacted with a surface modifier after attrition.

A general procedure for preparing the particles of this invention is set forth below. The NSAID selected is obtained commercially and/or prepared by techniques known in the art in a conventional coarse form. It is preferred, but not essential, that the particle size of the coarse NSAID selected be less than about 100 µm as determined by sieve analysis. If the coarse particle size of the NSAID is greater than about 100 µm, then it is preferred that the particles of the NSAID be reduced in size to less than 100 µm using a conventional milling method such as airjet or fragmentation milling.

The coarse NSAID selected can then be added to a liquid medium in which it is essentially insoluble to form a premix. The concentration of the NSAID in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 1000 nm. It is preferred that the premix be used directly when a ball mill is used for attrition. Alternatively, the NSAID and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the NSAID conveniently can take the form of a dispersion mill. Suitable dispersion mills include a ball mill, an attritor mill, a vibratory mill, a planetary mill, media mills such as a sand mill and a bead mill. A media mill is preferred due to the relatively shorter milling time required to provide the intended result, i.e., the desired reduction in particle size. For media milling, the apparent viscosity of the premix preferably is from about 10 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, polymeric grinding media and zirconium oxide, such as 95% ZrO stabilized with magnesia, zirconium silicate, and glass grinding media provide particles having levels of contamination which are believed to be acceptable for the preparation of pharmaceutical compositions. Further, other media, such as stainless steel, titania, alumina, and 95% ZrO stabilized with yttrium, are expected to be useful. Preferred media have a density greater than about 2.5 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the NSAID. Processing temperatures of less than about 30°–40° C. are ordinarily preferred. If desired, the processing equipment can cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

Milling must be carried out under acidic conditions, at a pH of from 2–6, preferably 3–5. The preferred pH depends, e.g., on the acidity and solubility of the particular NSAID selected. Acid resistant milling equipment is highly preferred, e.g., equipment fabricated of high grade stainless steel, e.g., grade 316 SS, or equipment coated with an acid resistant coating.

The surface modifier, it if was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80kHz for time of about 1 to 120 seconds.

The relative amount of the NSAID and surface modifier can vary widely and the optimal amount of the surface modifier can depend, for example, upon the particular NSAID and surface modifier selected, the critical micelle concentration of the surface modifier if it forms micelies, the surface area of the NSAID, etc. The surface modifier preferably is present in an amount of about 0.1–10 mg per square meter surface area of the NSAID. The surface modifier can be present in an amount of 0.1–90%, preferably 0.5–80%, and more preferably 1–60% by weight based on the total weight of the dry particle.

The resulting dispersion is stable and consists of the liquid dispersion medium and the above-described particles. The dispersion of surface modified NSAID nanoparticles can be spray coated onto sugar spheres or onto a pharmaceutical excipient in a fluid-bed spray coated by techniques well known in the art.

Pharmaceutical compositions according to this invention can include the composition described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the NSAID for treatment is effective to obtain a desired therapeutic response for a particular composition and method of administration. The selected dosage level therefore, depends upon the particular NSAID, the desire therapeutic effect, on the route of administration, on the desired duration of treatment and other factors.

It is a particularly advantageous feature that the pharmaceutical compositions of this invention exhibit reduced gastric irritation and/or more rapid onset of action as illustrated in the example that follows.

EXAMPLE

Example 1

Preparation 1

To 670 g of deionized water, 30 g of hydroxypropylcellulose (Klucel Type EF; Aqualon) was dissolved using a continuous laboratory mixer. 300 g of naproxen was dispersed into the HPC solution until a homogeneous suspension was obtained. A laboratory scale media mill filled with polymeric grinding media was used in a continuous fashion until the mean particle size was approximately 200 nm as measured by laser light scattering technique, ex. Microtrak UPA.

Preparation 2

The 30% w/w naproxen dispersion prepared above was spray dried to a dry powder form using a laboratory spray drier equipped with a rotary atomizer. The final powder consisted of particles in the size range of 20–40 micron diamter and a moisture content of approximately 0.3% by LOD. The powder was hand filled into size 00 gelatin capsules to a strength of 250 mg naproxen/capsule. 220 g of the spray dried material above was blended prepared with 44 g of croscarmellose sodium (Ac-Di-Sol) in a small twin shell blender. The material was passed through a roller compactor at 10 tons pressure and mill/sieve to approximately 16–40 mesh particle size. 134 g of lactose (hydrous) and 2 g of magnesium stearate was blended with the dry granulation for 15 minutes in a twin shell blender. The powder was compressed on a rotary tablet press to a final tablet weight of 400 mg and a hardness of 9–12 kp. Each tablet contained 200 mg of naproxen. The nanonaproxoflin was tested for adsorption time spiral co? tablets in fed dogs. The following was found.

| Bioavailability Results in Fed Dogs | | |
| --- | --- | --- |
| Formulation | Dose* | MAT** |
| Preparation 1 | 250 | 9 |
| Preparation 2 | 250 | 11 |
| Example 1 | 200 | 14 |
| Anaprox Caplet (Syntex) | 250 | 45 |
| ALEVE Caplet (Proctor and Gamble) | 200 | 40 |
| Naproxsyn suspension (Syntex) | 250 | 49 |

*mg of naproxen per dog
**MAT = mean-absorption time in minutes (n = 4–9)

We claim:

1. Particles consisting essentially of an NSAID having hydroxypropyl cellulose adsorbed on the surface thereof in an amount sufficient to maintain an average particle size of less than about 1000 nm, wherein said NSAID is selected from nabumetone, tiaramide, proquazone, bufexamac, flumizole, epirazole, tinoridine, timegadine, dapsone, aspirin, diflunisal, benorylate, fosfosal, diclofenace, alclofenac, fenclofenac, etodolac, indomethacin, sulindac, tolmetin, fentiazac, tilomisole, carprofen, fenbufen, flurbiprofen, ketoprofen, oxaprozin, suprofen, tiaprofenic acid, ibuprofen, naproxen, fenprofen, indoprofen, piroprofen, flufenamic, mefenamic, meclofenamic, niflumic, oxyphenbutazone, phenylburzone, apazone and feprazone, piroxicam, sudoxicam, isocam and tenoxicam.

2. The particles of claim 1 having an effective average particle size of less than 400 nm.

3. The particles of claim 1 wherein the hydroxypropyl cellulose is present in an amount of 0.2 to 90% by weight based on the total weight of the dry particle.

4. A method of preparing the particles of claim 1 comprising the steps of dispersing an NSAID and hydroxypropyl cellulose in a liquid dispersion medium and wet grinding said NSAID in the presence of rigid grinding media to an effective average particle size of less than about 1000 nm, wherein the pH of said medium is maintained within the range of from 2 to 6 during said wet grinding.

5. The particles of claim 1 wherein said NSAID is selected from naproxen, indomethacin and ibuprofen.

6. The particles of claim 5 wherein said NSAID is naproxen.

7. The particles of claim 1 wherein said hydroxypropyl cellulose has a viscosity range from 1 to 100 cps.

8. A pharmaceutical composition comprising the particles of claim 1 and a pharmaceutically acceptable carrier.

9. A method of treating a mammal comprising administering to the mammal an effective amount of the pharmaceutical composition of claim 1.

10. A method of reducing gastric irritation following oral administration to a mammal of a pharmaceutical composition comprising an NSAID, said method comprising administering said pharmaceutical composition in the form of particles consisting essentially of said NSAID having hydroxypropyl cellulose adsorbed thereon in an amount sufficient to maintain an average particle size of less than about 1000 nm.

11. A method of hastening onset of action following administration to a mammal of a pharmaceutical composition comprising an NSAID, said method comprising administering said pharmaceutical composition in the form of particles consisting essentially of said NSAID having hydroxypropyl cellulose adsorbed thereon in an amount sufficient to maintain an average particle size of less than about 1000 nm.

* * * * *